United States Patent
Bachhuber et al.

[19]

[11] Patent Number: 6,062,090

[45] Date of Patent: May 16, 2000

[54] APPARATUS AND METHOD FOR DETERMINING THE STRENGTH AND TYPE OF SOIL

[75] Inventors: Carl G. Bachhuber; Steven M. Luna, both of Pueblo, Colo.

[73] Assignee: Transportation Technology Center, Inc., Pueblo, Colo.

[21] Appl. No.: 08/933,736

[22] Filed: Sep. 23, 1997

Related U.S. Application Data

[63] Continuation-in-part of application No. 08/688,713, Jul. 31, 1996, abandoned.

[51] Int. Cl.⁷ ...................................................... G01N 3/00
[52] U.S. Cl. ............................................................ 73/784
[58] Field of Search ........................................ 73/84, 784

[56] References Cited

U.S. PATENT DOCUMENTS

| | | |
|---|---|---|
| 3,906,781 | 9/1975 | Vlasblom . |
| 3,958,646 | 5/1976 | Saint-Remy Pellissier . |
| 3,964,298 | 6/1976 | Saint-Remy Pellissier . |
| 3,988,923 | 11/1976 | Elmiger et al. ............................. 73/84 |
| 3,999,424 | 12/1976 | Saint-Remy Pellissier . |
| 4,332,160 | 6/1982 | Baragar et al. . |
| 4,393,691 | 7/1983 | Koehne . |
| 4,398,414 | 8/1983 | MacGregor .................................. 73/84 |
| 4,594,885 | 6/1986 | Rodger ........................................ 73/84 |
| 5,125,266 | 6/1992 | Ingram et al. . |
| 5,313,825 | 5/1994 | Webster et al. . |
| 5,339,679 | 8/1994 | Ingram et al. . |

FOREIGN PATENT DOCUMENTS

| | | |
|---|---|---|
| 1239499 | 4/1967 | Germany . |
| 291-641 | 7/1991 | Germany . |
| 369464 | 11/1973 | Russian Federation .................... 73/84 |
| 896-503 | 1/1982 | U.S.S.R. . |

*Primary Examiner*—Robert Raevis
*Attorney, Agent, or Firm*—Dorr, Carson, Sloan & Birney, P.C.

[57] ABSTRACT

A novel method and apparatus for measuring the dynamic loading characteristics of a soil bed is provided. The invention pertains to a method and apparatus for measuring, as a function of time, the resistance to penetration offered by a soil bed as the apparatus is fed into the soil at a constant rate. The device of the invention measures and records the multidirectional forces exerted upon it as it is fed through varying layers and types of soil in order to determine the types of soil encountered, their resistance to leading forces, and their various thicknesses and compositions. The device and method are particularly useful for testing and evaluating the bed surfaces of railroads and highways.

15 Claims, 5 Drawing Sheets

APPARATUS AND METHOD FOR DETERMINING THE STRENGTH AND TYPE OF SOIL

This is a continuation-in-part of application Ser. No. 08/688,713, filed on Jul. 31, 1996, now abandoned, which was abandoned upon the filing hereof.

BACKGROUND OF THE INVENTION

The present invention relates to a novel method and apparatus for measuring the dynamic loading characteristics of a soil bed. More particularly, the invention concerns a method and apparatus for measuring, as a function of time, the resistance to penetration offered by a soil bed as the apparatus is fed into the soil at a constant rate. Even more particularly, the device measures and records the multidirectional forces exerted on the device as it is fed through several layers and types of soil in order to determine the types of soil involved, their resistance to loading forces, and their various thicknesses.

Uneven settlement of railroad track due to weak subgrade support is a well-known problem in the railroad industry. (See Chrismer et al., *International Symposium on Cone Penetration Testing*, Oct. 4–5, 1995, which is incorporated herein by reference.) In response to the settlement of track, railroads frequently implement remedial measures without knowing the cause of the track failure or the precise condition of the substructure beneath the track. Such remedial measures may include the placement of hot mix asphalt beneath the ballast layer—the top granular layer closest to the track—but above the subgrade, or lifting the track to tamp additional ballast under the railroad ties. If the cause of the failure is not properly diagnosed, an ineffective, and frequently costly, repair may be undertaken.

In addition, the maximum permissible axle load on North American railroads was increased in recent years from thirty-three to thirty-nine tons, thereby necessitating reinforcement of weak sections of track. Frequently, however, weak subgrade support does not manifest itself immediately in the form of track settling, and may not, as a result, be immediately evident.

Cone penetrometers have been employed for more than two decades in the testing of the characteristics of soil beds. Examples of two such devices are shown in U.S. Pat. No. 5,125,266, issued to Ingram et al. on Jun. 30, 1992, and U.S. Pat. No. 4,398,414, issued to MacGregor on Aug. 16, 1983, both of which are incorporated herein by reference. One problem associated with existing penetrometers has been the weakness of the cone used to initially penetrate the soil. The cones on previous devices have been constructed of materials and to specifications which make them ill-suited to withstand the repeated pushing through an extremely hard ballast layer that has been compacted by many years of train traffic. In some instances, the pushing force exerted on the cone upon entry into the ballast layer may approach 10,000 pounds per square inch (psi). Existing cones have been known to dent, bend, or otherwise fail when subjected to continually strenuous conditions over a period of time.

Some known devices have attempted to solve the problem of cone durability by employing a cone constructed of extremely hard materials. Many of these devices have also utilized cones with particularly thick outer layers or wide outer dimensions. These strategies have frequently yielded a more durable cone, but at the expense of measurement sensitivity. Cones having a thick outer layer and constructed of the hardest materials are unable to measure accurately the forces being exerted on them due to their decreased sensitivity to such forces.

Inaccuracies associated with many of the prior art devices can be attributed, in large part, to the devices' measurement of resistance at the tip of the cone only. Such devices have also produced inaccurate force measurements due to their inability to compensate for any displacement or shifting of the penetrometer device which may occur during insertion into the ground and may be caused by the presence of rocks or particularly hard soil in the path of the device. Further, methods used for testing the resistance of soil beds to loading forces have involved driving the penetrometer device into the ground at a variable rate of speed, thereby increasing the probability of inaccurate force measurements.

Existing devices that have attempted to increase accuracy of soil detection by measuring forces on both the tip of the cone and along the sides of the device have frequently employed a gauge-type layout to sense these forces and to transmit data associated with the forces experienced. The force measurements of these devices, however, have typically been subject to "cross-talk," i.e., interference between the gauges measuring the friction force and those measuring tip resistance. Such interference occurs due to the wiring together of the two sets of gauges such that the measurements from the two may become indistinguishable.

OBJECTS OF THE INVENTION

Recognizing the need for an improved system for detecting the strength and type of soil in a given location, it is, therefore, an object of this invention to provide a novel, durable apparatus and method for measuring the dynamic loading characteristics of a soil bed which will withstand the strenuous demands of repeated pounding through the hard ballast surface layer of the soil.

Another object of this invention to provide a cone penetrometer device able to compensate for any shifting and/or displacement that may occur during the insertion of the device into extremely hard surfaces.

Yet another object of this invention is to provide a device for accurately measuring, recording, and analyzing the forces exerted on the tip of the device, along with the friction forces present along the exterior surface of the device, during its passage through various layers of soil.

A further object of the invention is to provide a method and device for determining the strength and type of a soil by passing the device through the soil at a constant rate, measuring the forces present on the device as a function of time during its passage through the soil, comparing the force measurements to those which would characterize known soil types, and matching the force measurements with those of a known soil type.

DETAILED DESCRIPTION OF THE PREFERRED EMBODIMENTS

The present invention relates to an apparatus and method for measuring the dynamic loading characteristics of a soil bed. In particular, the device of the present invention may be used to bore through several layers and types of soil and measure the resistive forces exerted on the device by the various soils. In this way, the measurements may then be compared to the characteristics of known types of soil in order to determine the soil types and their thicknesses encountered by the device. The cone penetrometer of the present invention may be used in analyzing soil content and strength beneath railroad tracks, as well as in numerous other applications.

Figure 1:
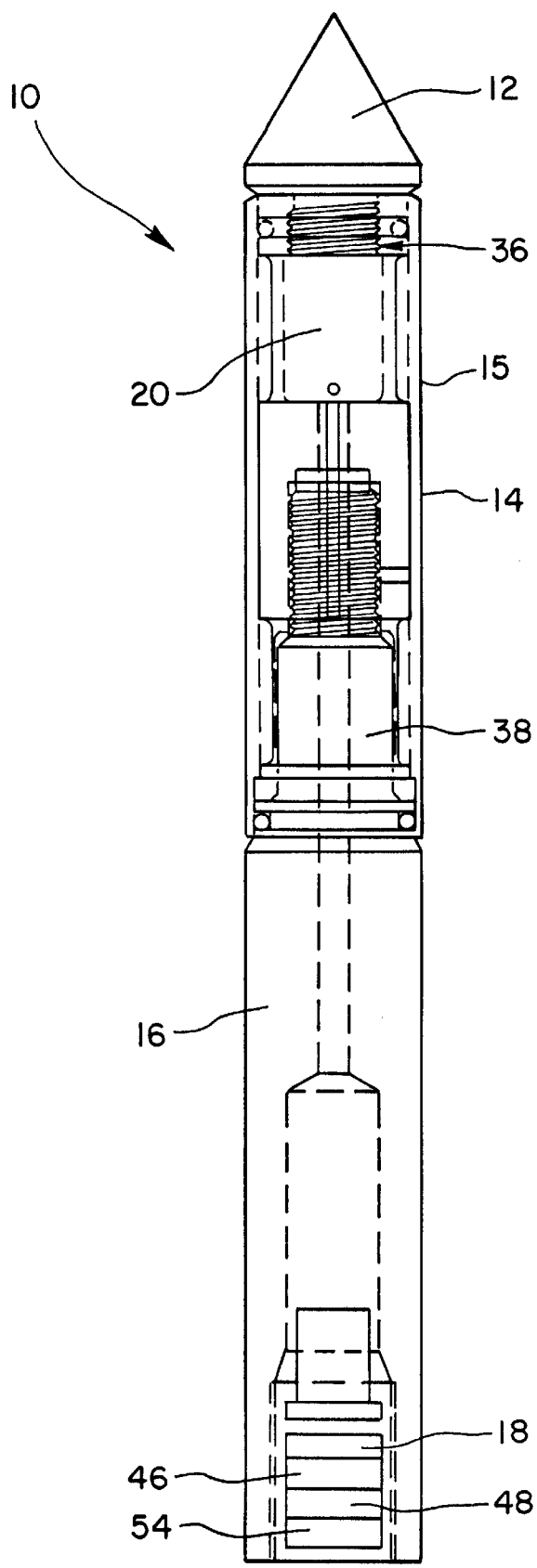
FIG. 1 is a partial longitudinal section view showing the cone portion, the first and second load cell arrangements including strain gauges, and the friction sleeve.
Figure 3:
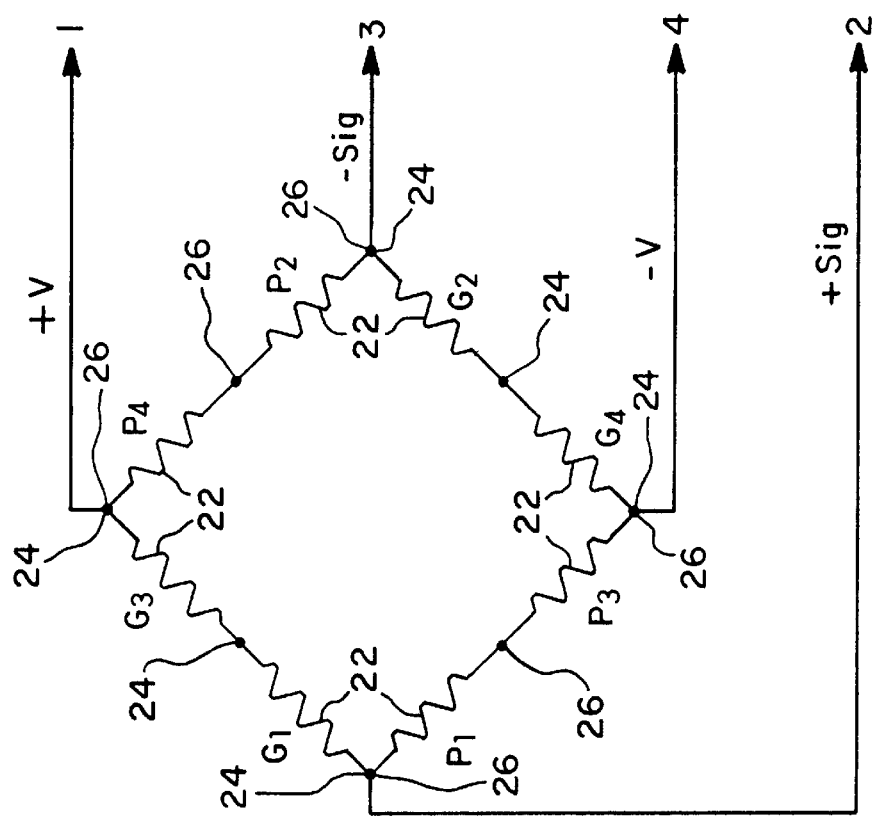
FIG. 3 is a circuit diagram showing the separate wiring of each strain gauge pair associated with the cone portion, and the path of the signals received by each gauge.
Figure 2A:
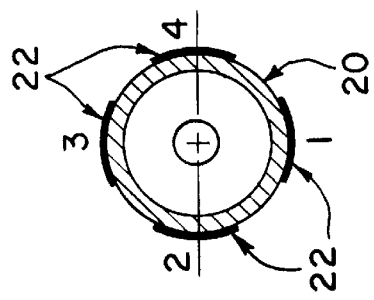
FIG. 2A is a sectional view taken along the line 2A—2A in FIG. 2.
Figure 2:
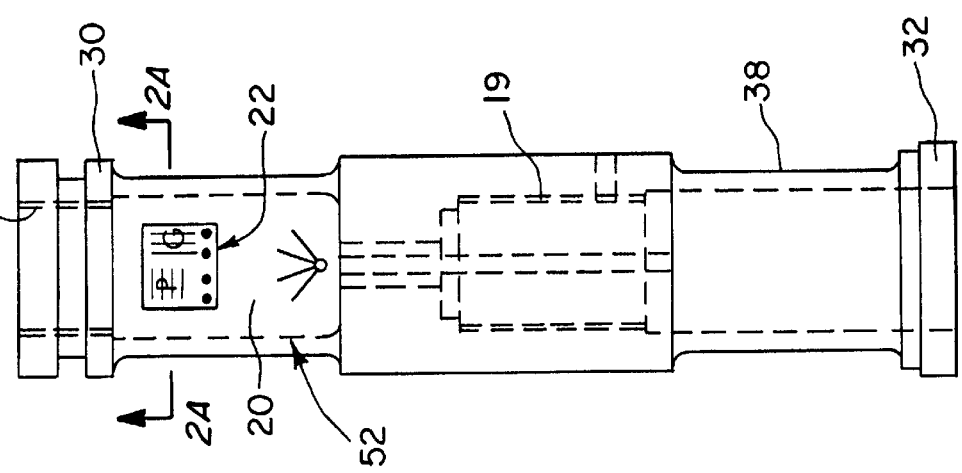
FIG. 2 is a partial longitudinal view illustrating the housing portion, and the location of the strain gauges associated with the cone portion and located within the housing portion.
Figure 4:
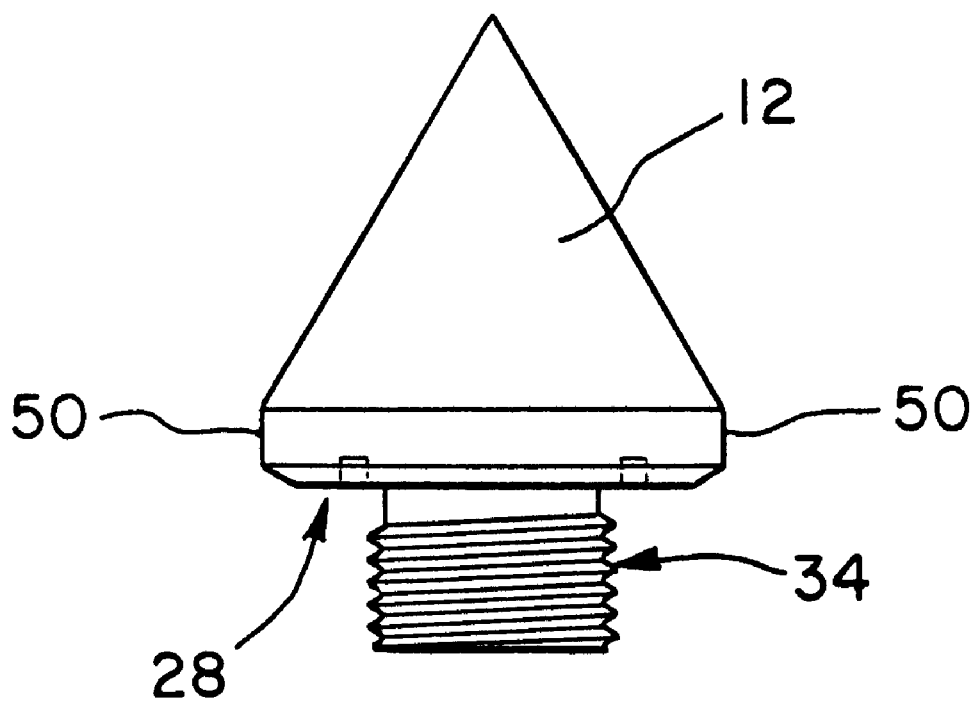
FIG. 4 is a partial view of the cone portion, illustrating the presence of threads for attachment to the housing portion.

Referring to FIGS. 1, 2, and 4, shown is a cone penetrometer 10 according to this invention. The penetrometer 10 consists of a conically-shaped boring portion 12, a sleeve 16, dual load cells 20 and 38, a housing portion 14, friction sleeve 15, computing means 48, and recording means 18. Male threads 17 of sleeve 16 engage female threads 19 of housing 1A. Load cell 20 consists of a plurality of strain gauges 22 having first ends 24 and second ends 26 (FIG. 3); in a preferred embodiment of the present invention, eight strain gauges 22 are used. The strain gauges 22 are preferably arranged in pairs P, G around the load cell 20 with one of the pair oriented along the longitudinal axis and one of the pair oriented along the annulus (FIG. 2A). For the most effective measurement of the forces exerted on the boring portion 12, the pairs of strain gauges 22 should be positioned at approximately ninety-degree intervals around the load cell 20. FIG. 3 illustrates the pairs of strain gauges 22 receiving signals based on the forces experienced by the boring portion 12. The use of four pairs of strain gauges 22 is, in no way, however, to be construed as a limitation of the present invention. More accurate measurements of the forces experienced by the boring portion 12 during its passage through a soil bed may, in fact, be obtained through the use of more pairs of strain gauges 22. The strain gauges 22 are wired in such a way that each pair possesses one strain gauge 22 dedicated to measuring the vertical force exerted on boring portion 12 and one strain gauge 22 dedicated to measuring the resultant horizontal force generated by vertical force.

Figure 6:
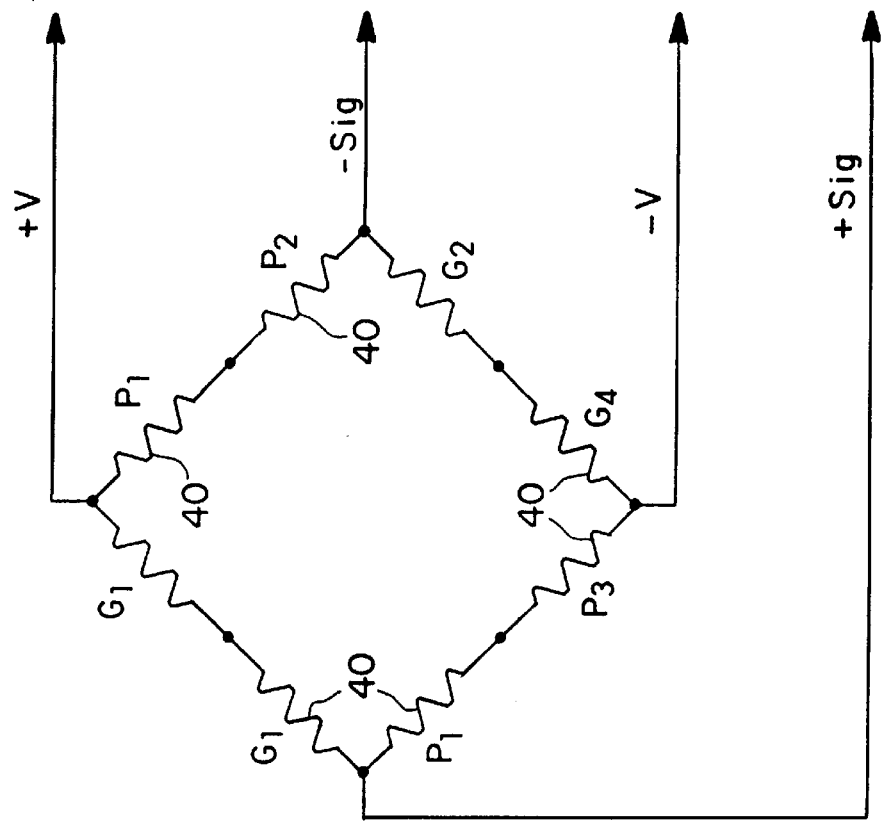
FIG. 6 is a circuit diagram showing the separate wiring of each strain gauge associated with the friction sleeve, and the path of the signals received by each gauge.
Figure 5:
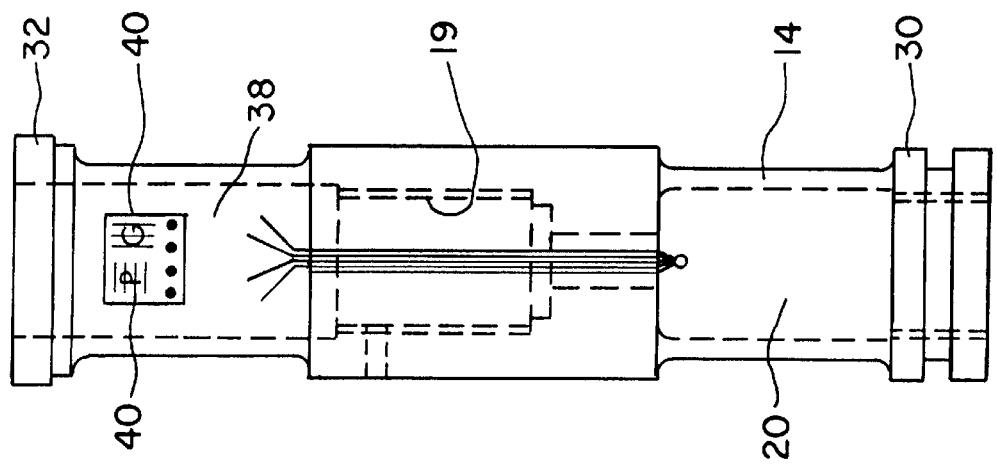
FIG. 5 is a partial longitudinal view illustrating the housing portion, shown inverted as compared to FIG. 2, showing the location of the strain gauges associated with the friction sleeve and located within the housing portion.

As discussed above, the strain gauges 22 are arranged in order to receive signals corresponding to the tip resistance experienced by the boring portion 12 as it passes through the medium. The first end 30 of housing portion 14 is connected to boring portion 12 by means of male threads 34 on boring portion 12, most clearly shown in FIG. 4, and female threads 36 on housing portion 14. A second load cell 38, most clearly depicted in FIG. 5, is connected to housing portion 14 and consists of a plurality of strain gauges 40. In a preferred embodiment of the present invention, eight strain gauges 40 are used. Friction sleeve 15 is slidably mounted over load cells 20 and 38, being held captive by end 32 and the boring portion 12. Strain gauges 40 are preferably arranged in pairs on all 38, similar to those on load cell 20. FIG. 6 shows the pairs of strain gauges 40 receiving signals based on the friction forces encountered by the friction sleeve 15 as it passes through the soil.

Electronically connected to first load cell 20 are first computing means 46 for receiving signals from first load cell 20 corresponding to the multiple and multidirectional forces being exerted on boring portion 12, and calculating the average force on boring portion 12 as a function of time. Second computing means 48 are electronically connected to second load cell 38 and are adapted to receive signals from second load cell 38 corresponding to the forces being exerted on friction sleeve 15, and compute the average force present on friction sleeve 15 at any moment in time. Recording means 18 are electronically connected to first computing means 46 and second computing means 48, and are adapted to receive and record the force measurements determined by first computing means 46 and second computing means 48. First computing means 46, second computing means 48, and recording means 18 may be located in any number of positions within penetrometer 10, and may even be positioned remotely from the device. In the preferred embodiment, however, the first computing means 46, second computing means 48, and recording means 18 are positioned within friction sleeve 15, as illustrated in FIG. 1.

Figure 7:
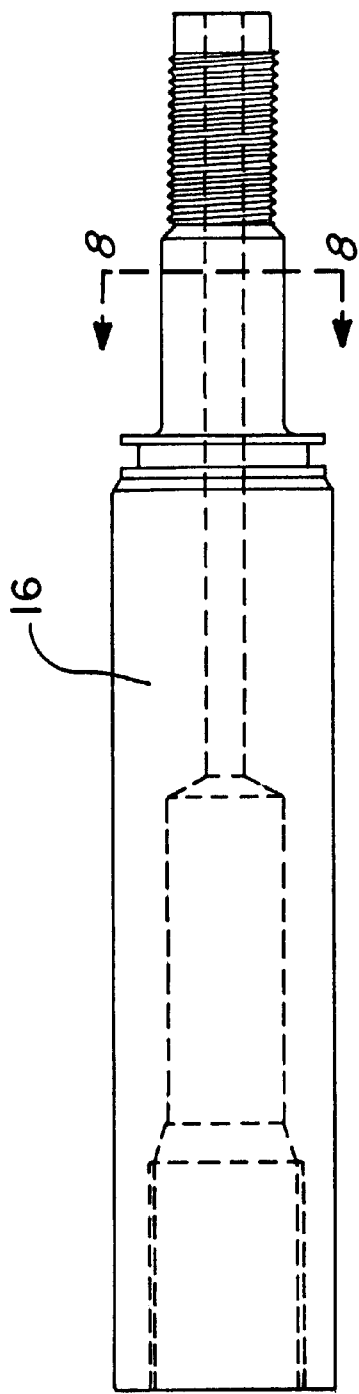
FIG. 7 is a partial longitudinal view of the friction sleeve.
Figure 8:
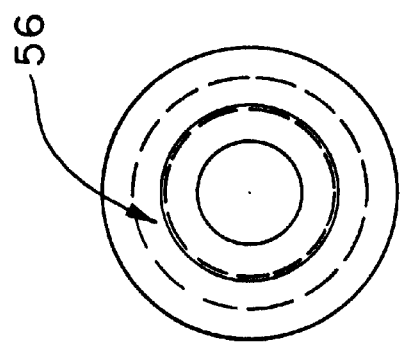
FIG. 8 is a sectional view taken along section lines 8—8 of FIG. 7.

In a preferred embodiment of the present invention, the boring portion 12 is solid, constructed of AISI 4150, 4340, or 4350 steel, and has an outside diameter of between 1.40 and 1.41 inches at its widest point 50, as shown in FIG. 4. The composition and dimensions of the boring portion 12 were chosen to maximize the durability of the boring portion 12 without sacrificing its sensitivity to force measurement. Further, the boring portion 12 is of sufficient weight and thickness as to resist much of the side-to-side jarring that would be experienced by lighter and thinner cones. Preferably, the housing portion 14 is constructed of AISI 4150, 4340, or 4350 steel, and has an outer wall 52 with a thickness of between 0.20 and 0.50 inches. The friction sleeve 15, as illustrated in FIGS. 7 and 8, may be constructed of AISI 4150, 4340, or 4350 steel, and has an outer wall 56 with a thickness of between 0.05 and 0.11 inches.

In operation, the penetrometer 10 is positioned above the area of soil desired to be tested. In the context of testing soil beneath railroad tracks, the penetrometer 10 can be transported along the tracks in a track-mobile vehicle and, upon arrival at the point to be tested, inserted into the ground by a hydraulic push frame or other powered apparatus mounted inside the track-mobile vehicle. In this way, the weight of the vehicle can be utilized as a reaction mass in helping to offset the resistance offered by the soil as the penetrometer 10 is driven into the ground.

As the cone penetrometer 10 is advanced preferably at a constant velocity through layers of soil, forces are exerted on the boring portion 12 by the ground. These forces are received electronically by the plurality of strain gauges 22 and transmitted to first load cell 20. Pairs of strain gauges 22 are connected to boring portion 12 such that each pair has one strain gauge 22 dedicated to measuring the vertical force and one strain gauge positioned and adapted to measure the horizontal force present on boring portion 12 at the point where the pair of strain gauges 22 is located. First computing means 46 associated with first load cell 20 are adapted to receive signals from first load cell 20. The orientation and interconnection of gauges 22 precludes load cell 20 from being affected by other than vertical forces. First computing means 46, upon receipt of the signals from first load cell 20, calculate the average vertical force exerted on boring portion 12 as a function of time.

Upon further insertion of the penetrometer 10 into the ground, the housing portion 14 and friction sleeve 15 contact the soil. As the penetrometer 10 is forced downward, the soil exerts forces on the friction sleeve 15, and strain gauges 40 receive and transmit data pertaining to these forces to the second load cell 38. In the preferred embodiment, eight strain gauges 40 are connected to load cell 38 connected by end 32 to friction sleeve 15. The use of four pairs of two strain gauges 40 is, however, not to be construed as a limitation of the invention. Preferably, these pairs of strain gauges 40 are connected around the friction sleeve 15 in approximately ninety-degree intervals. The strain gauges 40 associated with second load cell 38 are arranged with respect to friction sleeve 15 in such a way that each pair has one strain gauge 40 adapted to measure the vertical force caused by the frictional force on sleeve 15 and transmitted by end 32, and gage for measuring the resultant horizontal force caused by the vertical force on end 32. The gauges 40 are oriented such that only vertical frictional forces experienced by the friction sleeve 16 are received by the computing means 48 and one strain gauge 40 dedicated to measuring the horizontal force on friction sleeve 15 at the point where the pair of strain gauges 40 is located. Using the force data received from second load cell 38, second computing means 48 calculate the average vertical frictional force exerted on the friction sleeve 15 as a function of time.

In a preferred embodiment of the present invention, first computing means 46 and second computing means 48 electronically transfer all calculations to recording means 18 for recording and subsequent retrieval and analysis. In the most preferred embodiment, the data pertaining to the forces present on both the boring portion 12 and friction sleeve 15 as a function of time are fed into third computing means 54. Third computing means 54, which may be located within sleeve 15, elsewhere on penetrometer 10, or remotely from the system, is programmed to compare the force data with dynamic loading characteristics of known soil types. In this way, the types and thicknesses of soil layers encountered by penetrometer 10 during a given test may be determined. Once these soil characteristics are known to those responsible for maintaining the railroads, the proper repairs on the soil beneath the tracks can be accomplished.

The detailed description above is, in no way, intended to be exhaustive. It is envisioned that the apparatus and method may embody different types and styles of each element without departing from the spirit and scope of this invention.

What is claimed is:

1. An apparatus for determining the strength and type of soil, comprising:

a conically-shaped boring portion;

a substantially cylindrical housing portion connected to said boring portion;

a first load cell within said housing portion and adapted to generate a first signal corresponding to only vertical force on said boring portion as a function of time, said first load cell including a pair of strain gauges oriented such one gauge of the pair measures vertical forces and the other gauge of the pair measures resulting horizontal force generated by the vertical forces, whereby only the vertical forces are included in said first signal;

a friction sleeve slidably mounted within said housing portion;

a second load cell connected to said housing and adapted to generate a second signal corresponding to a vertical force on said friction sleeve as a result of friction as a function of time, said second load cell including a pair of strain gauges oriented such that one gauge of the pair measures the vertical frictional force on the friction sleeve and the other gauge of the pair measures resulting horizontal force on the friction sleeve, whereby only the vertical friction force is included in said second signal;

computing means for receiving said first signal and calculating the average vertical force on said boring portion and for receiving said second signal and calculating the average vertical force on said friction sleeve; and recording means for receiving and storing data from said computing means.

2. An apparatus as claimed in claim 1, wherein there are a plurality of said paired strain gauges that equals four and said paired strain gauges are arranged at approximately ninety degree intervals around said housing portion.

3. An apparatus as claimed in claim 1, wherein said second load cell comprises a plurality of paired strain gauges.

4. An apparatus as claimed in claim 3, wherein said plurality of said paired strain gauges equals four and said paired strain gauges are positioned to measure forces around the periphery of said friction sleeve.

5. An apparatus as claimed in claim 1, wherein said boring portion is constructed of steel and has a thickness of between 0.10 and 0.20 inches.

6. An apparatus as claimed in claim 1, wherein said friction sleeve is constructed of steel and has a thickness of between 0.05 and 0.11 inches.

7. An apparatus as claimed in claim 1, further comprising third computing means adapted to receive data from said recording means and to determine types and thicknesses of soil layers.

8. An apparatus for determining the strength and type of soil, comprising:

a conically-shaped boring portion;

a substantially cylindrical housing portion connected to said boring portion;

a first load cell within said housing portion and adapted to generate a first signal corresponding to multi-directional vertical forces on said boring portion as a function of time, said first load cell comprising a first set of paired strain gauges oriented such one gauge of a pair measures vertical forces and the other gauge of the pair measures resulting horizontal force generated by the vertical forces, whereby only the vertical forces are included in said first signal;

a friction sleeve slidably mounted within said housing portion;

a second load cell connected to said housing and adapted to generate a second signal corresponding to multi-directional frictional forces on said friction sleeve as a function of time, said second load cell comprising a second set of paired strain gauges oriented such that one gauge of a pair measures only the vertical frictional force on the friction sleeve and the other gauge of the pair measures resulting horizontal force on the friction sleeve, whereby only the vertical friction force is included in said second signal;

first computing means for receiving said first signal and calculating the average vertical force on said boring portion;

second computing means for receiving said second signal and calculating the average vertical friction force on said friction sleeve; and third computing means for receiving data from said first computing means and said second computing means, and calculating the strength and type of soil.

9. An apparatus as claimed in claim 8, wherein said first set of paired strain gauges comprises four paired strain gauges arranged at approximately ninety-degree intervals on said housing portion.

10. An apparatus as claimed in claim 8, wherein said second set of paired strain gauges comprises four paired strain gauges positioned to measure forces around the periphery of said friction sleeve.

11. An apparatus as claimed in claim 8, wherein said boring portion is constructed of steel and has a thickness of between 0.10 and 0.20 inches.

12. An apparatus as claimed in claim 8, wherein said friction sleeve is constructed of steel and has a thickness of between 0.05 and 0.11 inches.

13. A method for determining the strength and type of a soil layer, comprising the steps of:

attaching to a hydraulic push frame an electronic measuring device having a conically-shaped boring portion, first means for measuring vertical and horizontal resistance forces on said boring portion, second means for measuring vertical and horizontal friction forces around the periphery of said electronic measuring device, and recording means for recording said resistance forces and said friction forces;

lowering said electronic measuring device at an angle substantially perpendicular to the ground and at a substantially constant rate;

penetrating soil located beneath said hydraulic push frame;

measuring said resistance forces as functions of time while; and recording only said vertical resistance forces on said boring portion and said vertical friction forces on the measuring device.

14. A method as claimed in claim 13, wherein said electronic measuring device further comprises computing means for calculating the strength and type of soil, and said method further comprises calculating the strength and type of soil based on said resistance forces and said friction forces.

15. A method as claimed in claim 13, wherein said resistance forces comprise both compression forces and tension forces.

* * * * *

UNITED STATES PATENT AND TRADEMARK OFFICE
CERTIFICATE OF CORRECTION

PATENT NO.    : 6,062,090
DATED         : May 16, 2000
INVENTOR(S)   : Bachhuber et al.

It is certified that error appears in the above-identified patent and that said Letters Patent is hereby corrected as shown below:

<u>Column 4,</u>
Line 27, replace "sleeve 15" with -- sleeve 16 --.

<u>Column 5,</u>
Line 22, replace "friction sleeve 16" with -- friction sleeve 15 --.
Line 37, replace "sleeve 15" with -- sleeve 16 --.

Signed and Sealed this

Twenty-sixth Day of March, 2002

Attest:

JAMES E. ROGAN
*Attesting Officer*  *Director of the United States Patent and Trademark Office*